United States Patent [19]

Smirnov et al.

[11] 4,064,188
[45] Dec. 20, 1977

[54] METHOD OF DEHYDROGENATION, DEHYDROCYCLIZATION AND HYDRODEALKYLATION

[76] Inventors: Viktor Sergeevich Smirnov, Kutuzovsky prospekt, 26, kv. 555; Vladimir Mikhailovich Gryaznov, Leninskie Gory, MGU, Zona L, kv. 11; Valentina Ivanovna Lebedeva, Leninsky prospekt, 48a, kv. 29; Alexandr Petrovich Mischenko, Khersonskaya ulitsa, 7, korpus 4, kv. 115; Victoria Petrovna Polyakova, ulitsa Trofimova, 15, kv. 201; Evgeny Mikhailovich Savitsky, ulitsa Dm.Ulyanova, DNR-3, kv. 13, all of Moscow, U.S.S.R.

[21] Appl. No.: 755,598
[22] Filed: Dec. 30, 1976

Related U.S. Application Data

[60] Division of Ser. No. 578,659, May 19, 1975, which is a continuation of Ser. No. 434,224, Jan. 17, 1974, abandoned, which is a division of Ser. No. 271,186, July 12, 1972, Pat. No. 3,865,891, which is a division of Ser. No. 23,037, March 26, 1970, abandoned.

[51] Int. Cl.$^2$ .............................................. C07C 3/58
[52] U.S. Cl. ............................................. 260/672 R
[58] Field of Search ................................... 260/672 R

[56] References Cited

U.S. PATENT DOCUMENTS

| 3,562,346 | 2/1971 | Smirnov et al. | 260/672 R |
| 3,865,891 | 2/1975 | Smirnov et al. | 260/672 R |
| 3,931,345 | 1/1976 | Gryaznov et al. | 260/672 R |
| 3,950,447 | 4/1976 | Gryaznov | 260/672 R |
| 3,992,468 | 11/1976 | Cosyns et al. | 260/672 R |

Primary Examiner—Delbert E. Gantz
Assistant Examiner—C. E. Spresser
Attorney, Agent, or Firm—Holman & Stern

[57] ABSTRACT

Method for the dehydrogenation or dehydrocyclization of paraffins, for dehydrogenation of olefins with from 2 to 20 carbon atoms, and for hydrodealkylation of naphthalene homologs at temperatures ranging from 300° to 650° C on a catalyst comprising a palladium base alloy containing rhenium, tungsten or a combination of tungsten and ruthenium.

The method can find application in the production of monomers, such as isoprene, for synthetic materials, pharmaceuticals, in processing petroleum hydrocarbons and natural gas.

3 Claims, No Drawings

METHOD OF DEHYDROGENATION, DEHYDROCYCLIZATION AND HYDRODEALKYLATION

This is a divisional of application Ser. No. 578,659, filed May 19, 1975, which in turn is a continuation of application Ser. No. 434,224, filed Jan. 17, 1974, now abandoned, which in turn is a divisional of application Ser. No. 271,186, filed July 12, 1972, now U.S. Pat. No. 3,865,891 issued Feb. 11, 1975, which in turn is a divisional of application Ser. No. 23,037 filed Mar. 26, 1970, now abandoned.

The present invention relates to processing of hydrocarbons, and more particularly to a method of dehydrogenation or dehydrocyclization of paraffins, dehydrogenation of olefines with from 2 to 20 carbon atoms, and for hydrodealkylation of aromatic hydrocarbons, which are carried out either separately or simultaneously. Such method can find application when producing monomers for synthetic meterials, pharmaceuticals and other synthetic semiproducts, when processing petroleum hydrocarbons and natural gas, vegetable oils, and also for producting ultrapure hydrogen.

The known methods, industrially employed for processing hydrocarbons, use the catalysts in the form of blacks, powders and granules, comprising, as a rule, a mixture of two or more substances, or they are applied onto supports, for example, nickel, platinum onto aluminium oxide.

Such catalysts cannot be employed as membrane catalysts, that is, permselective for hydrogen, and they do not allow simultaneous running of dehydrogenation and hydrodealkylation processes without mixing the starting substances. These processes are more expedient to be carried out with the catalyst being used as a partition permselective for hydrogen only, so that on one side of the partition there should take place the process with elimination of hydrogen, and on the other side thereof, the process of addition of the hydrogen that has passed through the partition.

Earlier it has been proposed that palladium alloys comprising at least one of the rest of the elements belonging to group VIII of the Periodic System as well as copper, silver, gold or boron should be used as such a partition or "membrane catalyst" (cf. French Pat. No. 1,579,529).

The use of these catalysts has shown them to possess sufficiently high activity and selectivity for carrying out the processes.

An object of the present invention is to provide a method for the dehydrogenation or dehydrocyclization of olefins and for the hydrodealkylation of naphthalene homologs which is free of the aforementioned and other such disadvantages and, specifically, comprises contacting the feedstock with a catalyst based on palladium alloys which are highly thermostable and selectively permeable to hydrogen.

Said and other objects of the invention are accomplished by using a method for the dehydrogenation or dehydrocyclization of paraffins, dehydrogenation of olefins with from 2 to 20 carbon atoms, and for hydrodealkylation of naphthalene homologs at temperatures ranging from 300° to 650° C with a catalyst comprising a palladium base alloy containing a metal selected from the group consisting of rhenium, tungsten and combinations of tungsten and ruthenium, the content of palladium in said alloy being in the range of from 60 to 99 weight percent. The following combinations of the said components in the alloy are possible. An alloy comprising 80 to 99 weight percent of palladium and 1 to 20 weight percent of rhenium; a more specific composition is an alloy comprising 95 weight percent of palladium and 5 weight percent of rohenium. Other combinations of said components in the alloy are featured by an alloy comprising 80 to 99 weight percent of palladium and 1 to 20 weight percent of tungsten, and also by an alloy comprising 75 to 97.5 weight percent of palladium, 2 to 20 weight percent of tungsten and 0.5 to 5 weight percent of ruthenium.

A more specific composition of the alloy is that comprising 94 weight percent of palladium, 5 weight percent of tungsten and 1 weight percent of ruthenium.

Said catalysts can be used either in a conventional fashion, that is, as a powder or black, or a gauze, or, else, as partitions, such as membranes, films, foils and tubes which are permselective for hydrogen.

The introduction of rhenium or tungsten into the composition of the palladium alloy enhances the thermal stability of the catalyst, which is essential for the heat treatment of the catalyst in the process of its regeneration. Moreover, the processing of alkanes with the number of carbon atoms greater than six on these alloys makes it possible to obtain mainly benzene, obviating the stage of dealkylation of alkyl aromatics.

The introduction of ruthenium into the alloy comprising palladium and tungsten allows a material increase in the yield of isoprene when dehydrogenating 2-methylbutene 1.

The conversion process can be carried out either with the pure substances, or in a stream of helium or argon in a silica reactor, into which the catalyst is placed.

For a better understanding of the invention, some examples are given hereinabove by way of illustration. In all the examples that follow the rate of passage is 30 ml/min. The reaction products were analyzed chromatographically.

EXAMPLE 1

Dehydrogenation of 2-Methylbutene-1

Dehydrogenation of 2-methylbutene-1 to isoprene is carried out at a temperature ranging from 300° to 500° C. The catalyst is a foil made of palladium alloy comprising 5 weight percent of tungsten and 1 weight percent of ruthenium. The weight of the catalyst is 0.975 g, total surface area, 33 sq. cm.

Given in Table 1 below is a temperature dependence of the yield of isoprene and other reaction products in volume percent to the hydrocarbon passed.

Table 1

| t, °C | 2-Methylbutene-1, volume percent | 2-Methylbutene-2, volume percent | Isoprene, volume percent |
|---|---|---|---|
| 300 | 31.6 | 65.2 | 3.2 |
| 314 | 30.3 | 66.0 | 3.7 |
| 330 | 28.2 | 66.3 | 5.5 |
| 355 | 25.8 | 68.1 | 5.5 |
| 370 | 24.4 | 57.4 | 8.5 |
| 370 | 29.5 | 61.7 | 7.3 |
| 380 | 29.2 | 59.7 | 10.2 |
| 412 | 26.0 | 61.7 | 12.3 |
| 430 | 25.3 | 54.9 | 19.8 |
| 440 | 28.1 | 45.5 | 28.1 |
| 447 | 34.0 | 46.7 | 19.3 |
| 464 | 37.6 | 51.7 | 10.7 |
| 498 | 42.1 | 49.1 | 8.8 |

With the temperature rising from 300° to 440° C, the yield of isoprene increases and reaches 28.1 percent.

With a further increase of the temperature the yield of isoprene diminishes. The most optimal temperature is 440° C.

EXAMPLE 2

Dehydrogenation of Cyclohexane to Benzene

Dehydrogenation of cyclohexane to benzene is carried out at temperatures ranging from 300° to 500° C on the catalyst which is the palladium alloy including 5 weight percent of tungsten and 1 weight percent of ruthenium as stated in Example 1. Listed in Table 2 below is the yield of benzene depending on the temperature in the reactor.

Table 2

| t, °C | 300 | 330 | 343 | 394 | 403 | 411 | 416 | 430 | 492 |
|---|---|---|---|---|---|---|---|---|---|
| Benzene vol. % | 17.8 | 19.4 | 21.3 | 31.2 | 32.6 | 35.9 | 41.5 | 45.7 | 51.4 |

EXAMPLE 3

Dehydrocyclization of Heptane

Dehydrocyclization of heptane to toluene and benzene is carried out at temperatures ranging from 450° to 590° C on a foil catalyst made of the palladium alloy including 5 weight percent of tungsten and 1 weight percent of ruthenium as specified in Example 1.

Listed in Table 3 below is the yield of toluene, benzene and other reaction products in volume percent, depending on the temperature.

Table 3

| t, °C | Methane, vol. % | Hexane, vol. % | Heptane vol. % | Benzene vol. % | Toluene vol. % |
|---|---|---|---|---|---|
| 450 | 4.7 | — | 89.8 | 5.4 | traces |
| 460 | 8.3 | — | 82.7 | 9.0 | traces |
| 487 | 13.0 | — | 70.3 | 14.3 | 2.3 |
| 500 | 15.3 | — | 50.3 | 17.2 | 17.2 |
| 511 | 18.0 | — | 46.1 | 19.8 | 16.2 |
| 525 | 18.7 | traces | 45.2 | 21.6 | 14.5 |
| 553 | 19.4 | 3.1 | 38.1 | 21.5 | 18.0 |
| 570 | 20.6 | 2.1 | 38.7 | 21.8 | 16.8 |
| 577 | 23.1 | 0.5 | 27.0 | 33.9 | 16.0 |
| 580 | 28.6 | traces | 15.6 | 52.9 | 2.9 |
| 590 | 30.6 | — | 12.1 | 54.7 | 2.6 |

Maximum yield of aromatic hydrocarbons is attained at a temperature of 590° C, being 57.3 volume percent, including the yield of benzene which amounts to 54.7 volume percent.

EXAMPLE 4

Dehydrocyclization of Heptane

Dehydrocyclization of heptane to benzene and toluene is carried out at temperatures ranging frm 500° to 625° C. The catalyst is a foil from an alloy of palladium with 5 weight percent of rhenium. The weight of the catalyst is 3.31g, its total surface area is 55 sq. cm.

Given in Table 4 below is the temperature dependence of the yield of benzene and toluene in volume percent to the heptane passed.

Table 4

| t, °C | benzene vol. % | Toluene vol. % | Heptane vol. % | Other hydrocarbons vol. % |
|---|---|---|---|---|
| 549 | 10.5 | — | 89.4 | — |
| 588 | 21.9 | — | 70.2 | 8.0 |
| 605 | 29.6 | — | 58.3 | 12.1 |

Table 4-continued

| t, °C | benzene vol. % | Toluene vol. % | Heptane vol. % | Other hydrocarbons vol. % |
|---|---|---|---|---|
| 625 | 34.1 | 14.4 | 41.5 | 14.9 |

With an increase in the temperature, the yield of aromatic hydrocarbons becomes greater and reaches 48.5 volume percent at 625° C.

EXAMPLE 5

Dehydrocyclization of Octane

Dehydrocyclization of octane is carried out at temperatures ranging from 450° to 550° C, on a catalyst made of the palladium alloy with 5 weight percent of rhenium as specified in Example 4.

Listed in Table 5 below is the yield of benzene in volume percent, depending on the temperature in the reactor.

Table 5

| t, °C | Benzene vol. % | Octane vol. % | Other hydrocarbons vol. % |
|---|---|---|---|
| 455 | 2.9 | 97.0 | traces |
| 493 | 9.3 | 88.2 | 2.4 |
| 528 | 12.4 | 84.8 | 2.8 |
| 551 | 16.5 | 79.7 | 3.8 |

EXAMPLE 6

Hydrodealkylation of Toluene

Hydrodealkylation of toluene to benzene is carried out at temperatures ranging from 320° to 680° C. The catalyst is a foil of an alloy of palladium with 5 weight percent of rhenium. The weight of the foil is 3.31g; the total surface area is 55 sq. cm.

Listed in Table 6 below is the yield of benzene and other reaction products, in volume percent to the toluene passed, depending on the temperature conditions.

Table 6

| t, °C | $CH_4$ vol. % | $C_3H_8$ vol. % | Benzene vol. % | Toluene vol. % |
|---|---|---|---|---|
| 321 | 7.1 | 4.2 | 2.9 | 85.7 |
| 337 | 6.2 | 6.2 | 3.1 | 84.4 |
| 355 | 11.5 | 10.0 | 3.5 | 75.0 |
| 416 | 36.9 | 17.7 | 3.5 | 59.6 |
| 445 | 20.2 | 16.4 | 5.0 | 57.9 |
| 462 | 25.3 | 21.7 | 4.9 | 48.1 |
| 508 | 28.8 | 22.4 | 5.5 | 43.2 |
| 557 | 32.4 | 25.5 | 6.8 | 35.4 |
| 597 | 28.2 | 22.5 | 8.8 | 40.4 |
| 671 | 39.7 | 25.8 | 21.5 | 13.0 |

As can be seen from the Table, with an increase in the temperature the yield of benzene increases and reaches 21.5 volume percent at 671° C. Unlike the case with the catalysts proposed heretofore, (cf. French Pat. No. 1,579,529), on the alloy of palladium with rhenium the conversion of toluene to benzene is observed already at a temperature of 321° C.

EXAMPLE 7

Hydrodealkylation of 1,6-Dimethylnaphthalene

Hydrodealkylation of 1,6-dimethylnaphthalene to methylnaphthalenes and naphthalene is carried out at temperatures ranging from 461° to 624° C on a foil of an alloy of palladium with 5 weight percent of rhenium. The weight of the catalyst is 3.31g, total surface area is 55 sq. cm. The temperature dependence of the yield of naphthalene, α-methylnapthalene, β-methylnaphthalene and methane, in volume percent to the 1,6-dimethylnaphthalene passed, is listed in Table 7.

Table 7

| t, °C | $CH_4$ | Benzene and other hydrocarbons vol. % | Naphthalene vol. % | -Methylnaphthalene vol. % | -Methylnaphthalene vol. % | 1,6-Dimethylnaphthalene, vol. % |
|---|---|---|---|---|---|---|
| 461 | 10.5 | 3.0 | — | 1.6 | 1.3 | 83.6 |
| 505 | 20.6 | 3.1 | — | 2.6 | 3.6 | 70.1 |
| 568 | 16.4 | 2.1 | 3.8 | 8.1 | 12.9 | 56.7 |
| 610 | 13.9 | 2.2 | 1.2 | 3.8 | 7.9 | 70.7 |
| 624 | 19.8 | 3.5 | 5.7 | 7.6 | 10.2 | 53.7 |

The total yield of methylnaphthalenes and naphthalene reaches 24.8 percent at a temperature of 568° C.

EXAMPLE 8

Dehydrogenation of 2-Methylbutene-1

The catalysts used were palladium in an alloy with 5 weight pecent, 10 weight percent, and 15 weight percent of tungsten. The temperature of the dehydrogenation reaction was 445° C. The surface area of the catalyst samples made as foils was 62sq. cm. Listed in Table 8 below is the yield of isoprene, in volume percent when dehydrogenating 2-methylbutene-1, depending on the alloy composition.

Table 8

| Composition of Alloy | 5 Weight % of Tungsten | 10 Weight % of Tungsten | 15 Weight % of Tungsten |
|---|---|---|---|
| Isoprene | 4.2 | 5.3 | 8.2 |
| vol. percent | | | |

Thus, as can be seen from the disclosure, the new method proposed herein, as regards the activity and selectivity of catalysts are not inferior to, and in some cases even excel the catalysts proposed heretofore. Due to the fact, that said palladium alloys feature a greater thermostability, their application proves to be especially desirable in those cases when the processes are carried out at high temperatures, and in the course of regeneration the catalysts are subject to an intense heat treatment.

What is claimed is:

1. A method for the selective preparation of aromatic hydrocarbons by the hydrodealkylation of alkylaromatic hydrocarbons, which comprises the passing of a vaporized alkylaromatic hydrocabon feedstock at a temperature of 300° to 680° C over a catalyst in the form of a foil made of palladium alloyed with at least one member selected from the group consisting of rhenium, tungsten, and a combination of tungsten and ruthenium, the content of palladium in said alloy ranging from 60 to 99 weight percent.

2. A method for the hydrodealkylation of 1,6-dimethylnaphthalene according to claim 1 at temperatures ranging from 460° to 630° C on a catalyst in the form of a foil made of an alloy of 95 weight percent palladium and 5 weight percent rhenium.

3. A method for the hydrodealkylation of toluene according to claim 1 at temperatures ranging from 320° to 680° C on a catalyst in the form of a foil made of an alloy of 95 weight percent palladium and 5 weight percent rhenium.

* * * * *